United States Patent [19]

Tamm et al.

[11] Patent Number: 5,148,234
[45] Date of Patent: Sep. 15, 1992

[54] METHOD AND DEVICE FOR ANALYZING SAMPLES BY MEANS OF ATOMIC ABSORPTION SPECTROSCOPY

[75] Inventors: Rolf Tamm, Salem; Guenther Roedel, Owingen; Klaus Rogasch, Uhldingen-Muhlhofen, Fed. Rep. of Germany

[73] Assignee: Bodenseewerk Perkin Elmer GmbH, Uberlingen, Fed. Rep. of Germany

[21] Appl. No.: 681,240

[22] Filed: Apr. 5, 1991

[30] Foreign Application Priority Data

Apr. 7, 1990 [DE] Fed. Rep. of Germany ....... 4011338

[51] Int. Cl.[5] .......................... G01J 3/30; G01N 21/74
[52] U.S. Cl. ..................................... 356/312; 356/244
[58] Field of Search ............................... 356/312, 244

[56] References Cited

U.S. PATENT DOCUMENTS

| | | | |
|---|---|---|---|
| 3,591,289 | 7/1971 | Donega et al. | 356/312 |
| 4,098,554 | 7/1978 | Huber et al. | 356/312 |
| 4,840,484 | 6/1989 | Oishi et al. | 356/312 |
| 4,981,356 | 1/1991 | de Loos-Vollebergt | 356/244 |

FOREIGN PATENT DOCUMENTS 0356566 2/1988 European Pat. Off. .

Primary Examiner—F. L. Evans
Assistant Examiner—K. P. Hantis
Attorney, Agent, or Firm—Thomas P. Murphy; Edwin T. Grimes

[57] ABSTRACT

Method for analysis of samples by means of atomic absorption spectroscopy with electrothermal atomization of sample consists of the method steps: (a) introducing a liquid sample into a furnace, (b) heating the furnace up to a drying temperature for drying the sample, (c) subsequently heating the sample up to an atomizing temperature, in which a cloud of atoms develops in the furnace, in which cloud of atoms the components of the sample are present in atomic state, and (d) measurement of the atomic absorption of a measuring light beam with resonance spectral lines of an element looked for in the sample guided through the cloud of atoms. In this method (e), the vapors formed in the furnace during the heating of the furance up to the drying temperature are sucked off by a vacuum. Also, a device for carrying out this method is described.

19 Claims, 5 Drawing Sheets

METHOD AND DEVICE FOR ANALYZING SAMPLES BY MEANS OF ATOMIC ABSORPTION SPECTROSCOPY

TECHNICAL FIELD

The invention relates to a method for analyzing samples by means of atomic absorption spectroscopy with electrothermal atomization of the sample, with the method steps:

(a) introducing a liquid sample into a furnace,
(b) heating the furnace up to a drying temperature for drying the sample,
(c) subsequently heating the sample up to an atomizing temperature, at which a cloud of atoms develops in the furnace, in which cloud of atoms the components of the sample are present in atomic state, and
(d) measuring the atomic absorption of a measuring light beam directed through the cloud of atoms with resonance spectral lines of an element looked for in the sample.

Further, the invention relates to a device for carrying out such a method.

BACKGROUND ART

Atomic absorption spectroscopy is a very sensitive method for the quantitative analysis of a looked for element in a sample. A light source, e.g. a hollow cathode lamp, emits a light beam, which includes light with the line spectrum of a looked for element. The sample is atomized, i.e. an atomic vapor is formed, in which the elements of the sample are present in atomic state. The measuring light beam is directed through this atomic vapor. The absorption is measured, to which the measuring light beam is subjected in the atomic vapor. The concentration of the element looked for in the sample can be determined from this absorption after suitable calibration.

The atomization of the sample can occur by "electrothermal atomization". There, the liquid sample is introduced into a furnace. At first, the furnace is heated up to a drying temperature. The solvent vaporizes at this drying temperature. Subsequently a heating of the furnace up to a higher charring temperature occurs. Thereby, chemical compounds in the sample are split up. Also smoke can develop. Finally the furnace is heated up to an atomizing temperature, in which a "cloud of atoms" develops in the furnace, in which cloud of atoms the elements of the sample are present in atomic state. The measuring light beam is directed through this cloud of atoms.

Usually the furnace is a graphite tube. The electric current is passed through this graphite tube either through annular electrodes in longitudinal direction or through radial contact pieces in circumferencial direction. In order to protect the furnace made of graphite against the access of air and burning, at the high temperatures, the furnace is flown around inside and outside by an inert gas flow. This inert gas flow also carries away the vaporized solvent, during the drying process of the sample, and solid decomposition products, during the charring process.

It takes some time until the vaporized solvent and the decomposition products are carried away by the inert gas flow. Therefore, the drying and charring steps take undesirably long time. It is desired to shorten the time necessary for an analysis. Thereby, more analyses per hour can be made with one apparatus. Besides, the durability of a graphite furnace increases, if the graphite furnace is heated only for a short time for each analysis.

From European Published Patent Application No. 0,356,566 a method and a device are known for the electrothermal atomization of samples, in which device a sample liquid is vaporized by a "thermospray"-vaporizer and is guided into a graphite furnace as vapor jet. The graphite furnace is kept at a drying temperature. The sample condenses at the wall of the graphite furnace or a platform provided therein, while the vaporized solvent is sucked off by a vacuum. Thus the time for analyses can be shortened and the amount of the sample substance atomized with one analysis and thus the sensitivity can be increased. There, the graphite furnace is a longitudinally heated graphite tube, which is hold between annular contacts at its ends. The sucking-off of the solvent occurs through suction passages, which are formed in these contacts and are connected to a suction pump. There, a special arrangement with a thermospray-vaporizer is required.

DISCLOSURE OF THE INVENTION

It is an object of the invention, to shorten the time required for the anlyses, to extend the useful life of the furnace and to decrease the risk of cross contamination in a method of the type defined at the beginning.

According to the invention this object is achieved in that (e) the vapors developed in the furnace, while the furnace is heated up to the drying temperature, are sucked off by a vacuum.

Heating of the furnace up to a charring temperature can occur, in known way, between the heating of the furnace up to the drying temperature and sample atomization, at which charring temperature a decomposition of chemical compounds occurs in the sample, and a sucking-off of smoke and decomposition products by the vacuum can occur also during the heating of the furnace up to the charring temperature.

The invention can advantageously be realized in such a way, that for the generating of the vacuum, a suction tube is introduced through an opening into the furnace and is exposed to vacuum. There, the sample is introduced into the furnace through a sample introduction opening and the suction tube is introduced into the sample introduction opening as the said opening. The suction tube can be retracted from the opening while the furnace is heated up to an atomizing temperature and subsequently the atomic absorption is measured. In order to avoid cross contamination the suction tube can, following the measurement, again be introduced into the opening of the heated furnace for heating out. It is further advantageous, if the suction tube is exposed to the vacuum during the process of heating out.

A device for carrying out the method according to the invention, comprises (a) a tubular furnace for the electrothermal atomization of samples with a longitudinal bore and a central, lateral opening,
(b) means for passing a stepped electric current through the furnace,
(c) means for directing a measuring light beam through the longitudinal bore and a detector exposed to the measuring light beam,
(d) a suction tube arranged to be introduced into the furnace through the lateral opening,
(e) means for generating a vacuum in the suction tube, (f) a mechanism for introducing the suction tube into the opening of the furnace and for retracting the suction tube from the furnace and (g) a control device for coordinating the movement of the mechanism, the heating up of the graphite furnace and the means generating a vacuum.

Further, a rotary movement can be conferred to the suction tube by the mechanism after the suction tube has been retracted from the opening of the furnace, such that the opening lies open for the sample introduction when the suction tube is retracted.

An embodiment of the invention will now be described in greater detail with reference to the accompanying drawings.

PREFERRED EMBODIMENT OF THE INVENTION

Figure 1:
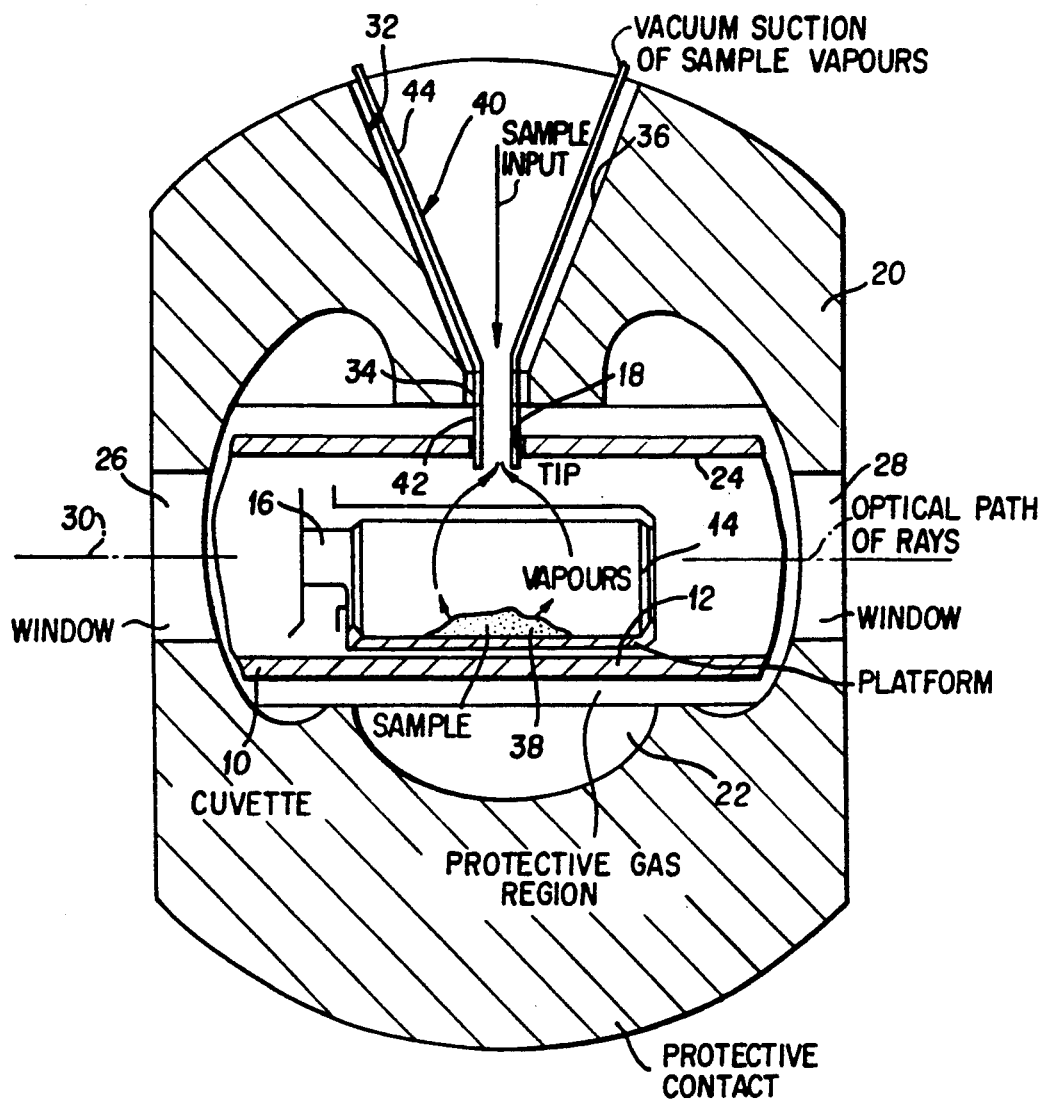
FIG. 1 is a longitudinal section of a transversely heated graphite furnace with a suction tube.

In FIG. 1 numeral 10 designates a transversely heated graphite furnace. The graphite furnace can be of the type disclosed in European Published Patent Application Number 0,326,642 or 0,350,722, for example. The graphite furnace has a tubular furnace body 12 and an integrated half-cylindrical platform 14. In the preferred embodiment the platform 14 is held at one end through a web 16. An opening 18 is provided opposite the platform 14 in the wall of the furnace body 12. The graphite furnace 10 is held with radial contact pieces (not illustrated) between two contacts. The contacts, from which one contact 20 can be seen in FIG. 1, form a cavity 22 closed to a large extent, in which cavity the graphite furnace is contained. An inert gas is introduced into this cavity through passages, which are formed in the contacts. The graphite furnace 10 has a longitudinal bore 24. Two windows 26 and 28 aligned with this longitudinal bore 24 are provided in the contact 20. The path of rays of the measuring light beam 30 extends through the windows 26 and 28 and the longitudinal bore 24. A funnel-like opening 32 is provided in the contact 20 at right angles to the longitudinal bore 24 and aligned with the opening 18 formed in the middle of the furnace body 12. The wall of the funnel-like opening 32 has a cylindrical section 34 adjacent to the cavity 22 and coaxial to the opening 18 of the graphite furnace 10 and a conically widening section 36 adjacent therto. A drop of sample 38 is applied to the platform 14 through the opening 32 and the opening 18.

In FIG. 1 the tip of a suction tube 40 is introduced into the opening 32 and 18. The tip of the suction tube 40 comprises a cylindrical section 42 and a funnel-like or conical section 44. The cylindrical section 42 projects coaxially through the section 34 of the opening 32 and through the opening 18 into the interior of the graphite furnace. The cylindrical section 42 ends directly opposite the drop 38 of the sample. The suction tube 40 is made of graphite.

Figure 2:
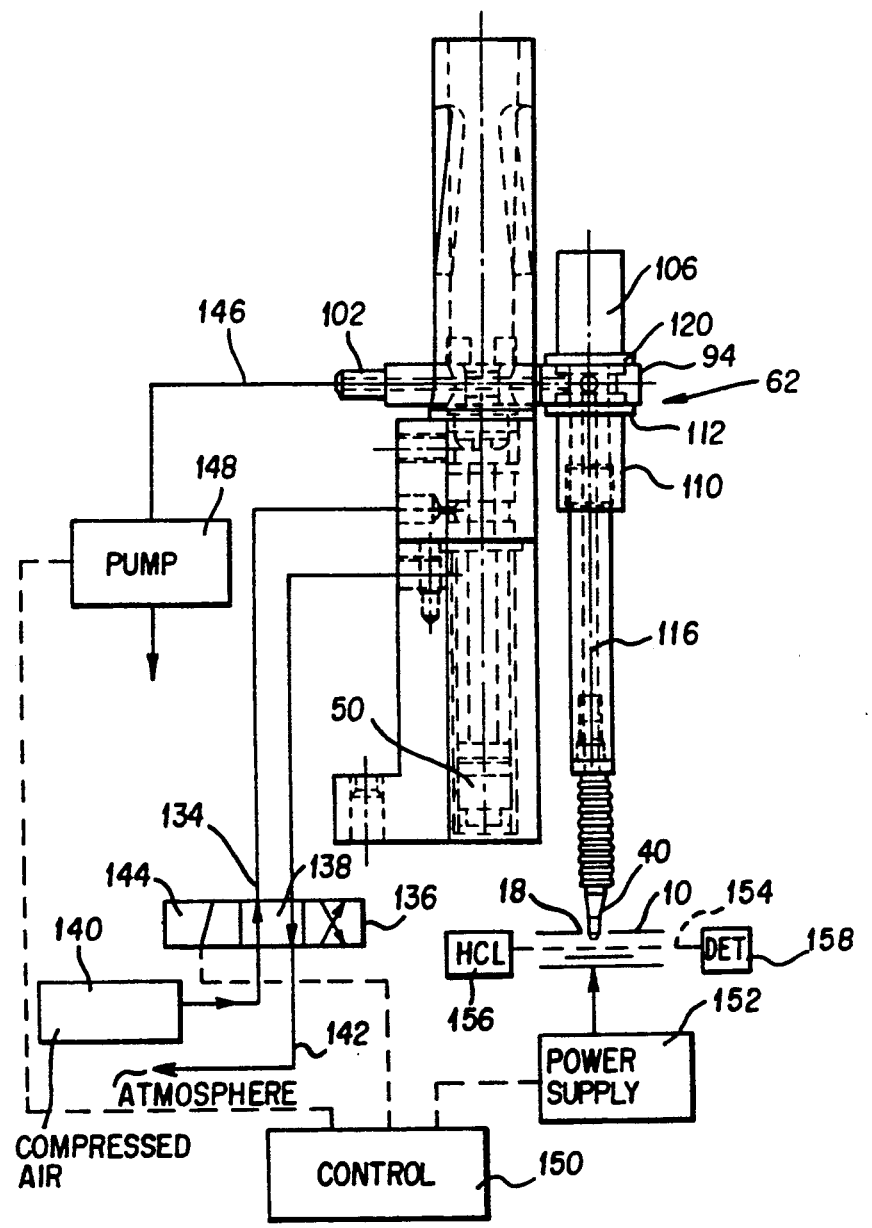
FIG. 2 is a side view of the suction tube and a mechanism for introducing the suction tube into the graphite furnace and for retracting the suction tube from the graphite furnace and further shows the control in schematic illustration.
Figure 3:
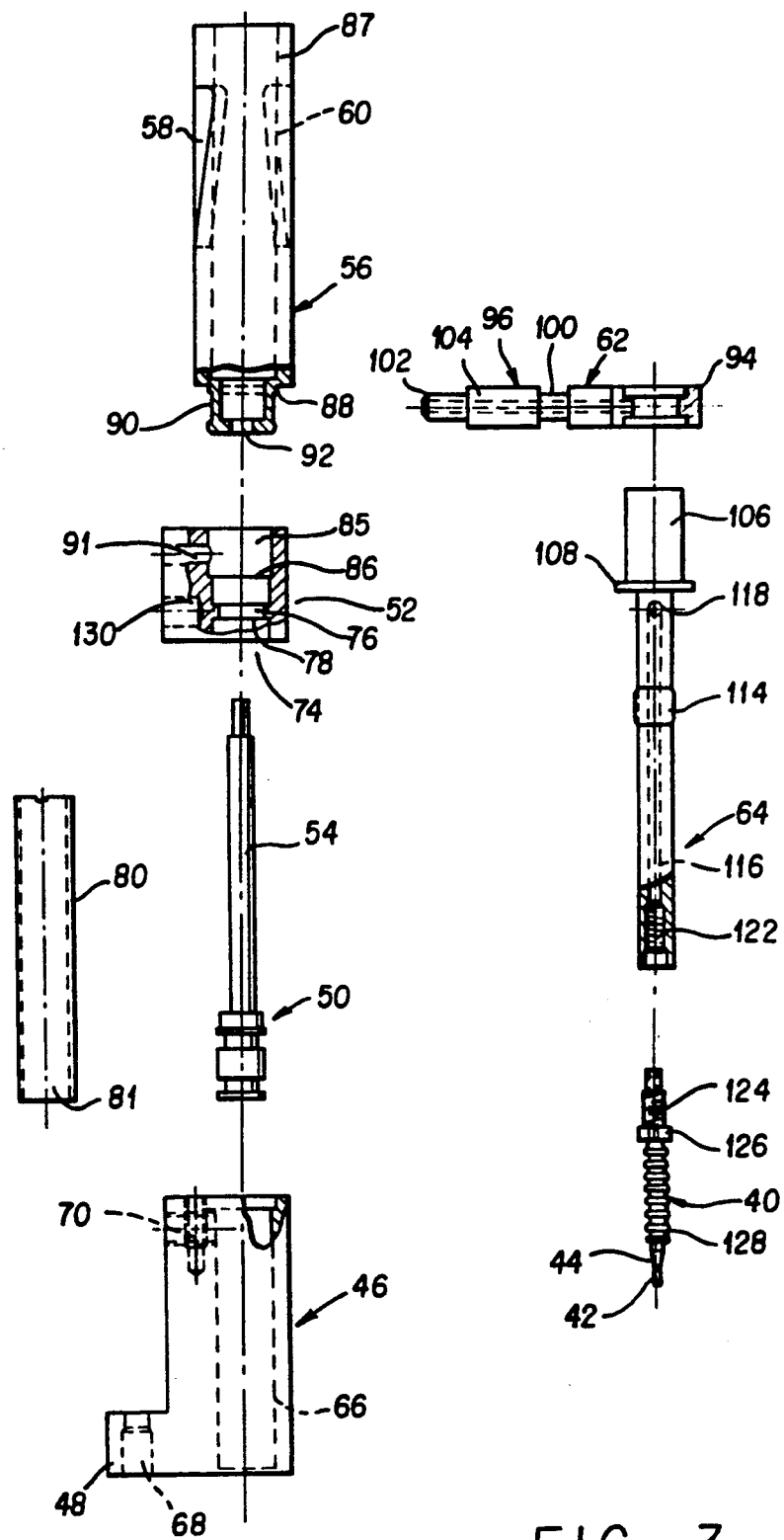
FIG. 3 is an exploded illustration and shows the suction tube and the particular components of the mechanism in detail.

In FIG. 2 and 3, the mechanism is illustrated, by which the suction tube 40 can be introduced into the opening 18 of the graphite furnace 10 and retracted from this opening 18. The mechanism comprises a cylinder housing 46. The cylinder housing 46 is screwed with a pedestal 48 on a plane surface of the furnace arrangement. A piston 50 is guided in the cylinder housing 46. The cylinder housing 46 is closed by a head piece 52. A piston rod 54 of the piston 50 projects through the head piece 52. A guiding sleeve 56 with two guiding slots 58 and 60 is located in the head piece. The guiding slots 58 and 60 are located diametrally opposite and are helically curved with large pitch in the same direction. A suction tube carrier 62 is guided in the guiding slots 58 and 60. The suction tube carrier 62 can be axially shifted in the guiding sleeve 56 by the piston rod 54. At the same time the suction tube carrier 62 is pivoted around the axis of the guiding sleeve 56 due the curvature of the guiding slots 58 and 60. The suction tube carrier 62 carries a suction tube portion 64, at the lower end of which the suction tube 40 is located. The piston 50 with the piston rod can pneumatically be moved up and down. The piston rod moves the suction tube carrier 62, which carries the suction tube portion 64 and the suction tube 40 provided thereon. During the upward movement, the suction tube carrier 62 with the suction tube portion 64 and the suction tube 40 are rotated away backwards due to the guiding slots 58 and 60, such that then the openings 32 and 18 are freely accessible for the introduction of sample.

In detail, the cylinder housing 46 comprises a bore 66. The pedestal 48 at the "lower" end of the cylinder housing 46 has a threaded bore 68 for fixing the cylinder housing 46 on a plane surface. The bore 66 is located a little unsymmetrically in the cylinder housing 46. Two threaded bores 70 and 72 are provided at the "upper" end face of the cylinder housing 46. These threaded bores 70, 72 permit the fixing of the head piece 52.

The head piece 52 has a bore 74. The bore 74 is also a little off-center to the head piece and coaxial to the bore 66 of the cylinder housing 46. The diameter of the bore 74 is a little smaller than the diameter of the bore 66. A bore 76 of smaller diameter is added to the bore 74. Thus an annular shoulder 78 is formed between the bores 74 and 76.

A cylinder sleeve 80 is located in the bore 74. The end face of the cylinder sleeve 80 engages the annular shoulder. The opposite end face of the cylinder sleeve 80 has sections 81. In this way, the cylinder sleeve 80 projects into the bore 74 and forms an annulus with the bore 74. The piston 50 is guided in the cylinder sleeve.

Bores aligned with the threaded 70 or 72, respectively, are provided beside the bore 74. Threaded bolts, which are screwed into the threaded bores 70 or 72, respectively, extend through these bores. Thereby, the head piece 52 is connected to the cylinder housing 46.

The head piece 52 has a stepped bore 85 adjacent to the bore 76 and coaxial with this bore, which stepped bore formes a shoulder 86. The guiding sleeve 56 is inserted into this stepped bore. The guiding sleeve 56 has a tubular sleeve portion 87, in which both of the steeply-helical guiding slots 58 and 60 are provided. The sleeve portion 87 is closed at its lower end in FIG. 3 by an edge 88 and a pot shaped portion 90 adjacent thereto and projecting downwards in FIG. 3. The "bottom" of the pot shaped portion 90 has a central aperture 92. The piston rod 54 is guided in this aperture 92. A radial threaded bore 91 is provided in the head piece 52 in the area of the bore 85. A clamping screw is screwed into this threaded bore 91, which clamping screw clamps the guiding sleeve 56 to the head piece 52.

The suction tube carrier 62 is guided in the guiding slots 58 and 60. The suction tube carrier 62 has an annular portion 94 and a integrate handle 96 adjacent thereto. The annular portion 94 has a collar on the inner side. The handle 96 is provided with a groove 100 and an end 102 of reduced diameter. A longitudinal passage 104 is formed in the handle 96, which passage starts from the inner wall of the annular portion 94 and ends in the end face of the handle 96. The groove and the end of the handle are guided in the guiding slots 58 and 60 of the guiding sleeve 56. The suction tube carrier 62 can be shifted in the guiding slots 58,60 by the piston 50 through the piston rod 54. If the suction tube carrier 62 is shifted upwards in FIG. 3, it is pivoted backwards about the axis of the guiding sleeve 62, at the same time, due to the steeply-helical form of the guiding slots.

A suction tube portion 64 is located in the suction tube carrier 62. The suction tube portion 64 is generally cylindrical and has a larger diameter head 106. A collar 108 is added to the head 106. The suction tube carrier 62 rests upon the annular portion 94 of the suction tube carrier 62 with the collar 108. A threaded sleeve 110 with a flange 112 is scewed on a thread 114 of the suction tube portion 64 and engages the annular portion 94 on the opposite side, at the bottom of FIG. 2. A longitudinal passage 116 extends in the suction tube portion 64. The longitudinal passage 116 is connected to the annulus 120 formed between the collar 108 and the flange 112 inside the tubular portion 94 through a transverse bore 118. The annulus 120 is sealed from atmosphere. The annulus is connected to the longitudinal passage 104 of the suction tube carrier 62.

The longitudinal passage 116 of the suction tube portion 64 widens at its end to a stepped threaded bore 122. The upper end 124 of the suction tube 40 provided with a thread is screwed into the threaded bore 122. The suction tube 40 is made of graphite. The suction tube 40 has a collar 126, which engages the end face of the suction tube portion 64. Further, the suction tube 40 has a section 128 provided with webs. A tip with the conical section 44 and the cylindrical section 42 (FIG. 1) is added to the section 128.

Figure 4:
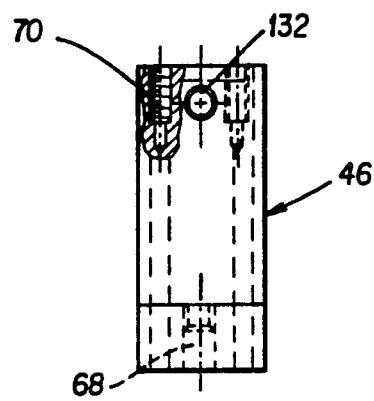
FIG. 4 is a view of the cylinder housing as viewed from the left in FIG. 3.
Figure 5:
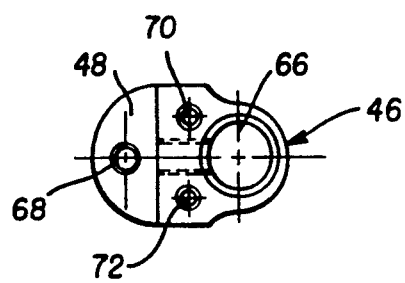
FIG. 5 is a plan view of the cylinder housing.
Figure 6:
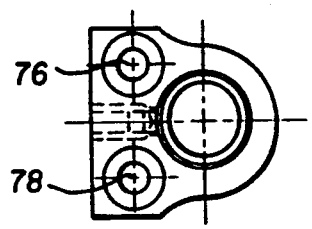
FIG. 6 is a plan view of a head piece, which is located on the cylinder housing of FIG. 4 and 5 and is screwed to this cylinder housing.
Figure 7:
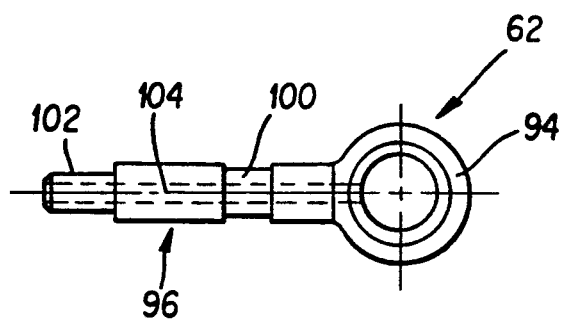
FIG. 7 is a plan view of a suction tube carrier in the mechanism of FIG. 2 and 3.
Figure 8:
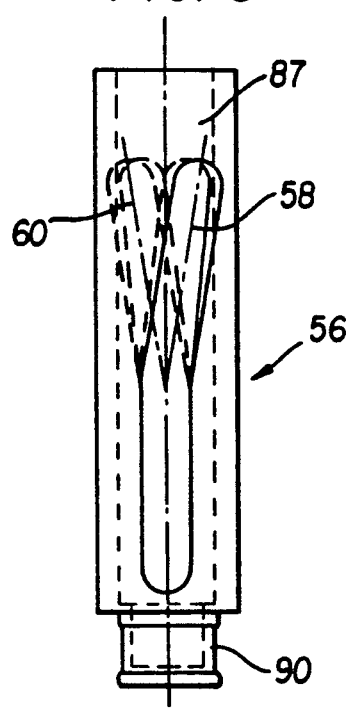
FIG. 8 is a side view of a guiding sleeve located on the head piece of FIG. 6 as viewed from the left in FIG. 3.

A radial bore 130 is provided in the head piece 52, which radial bore 130 forms a control pressure port. This bore 130 is connected to the interior of the cylinder sleeve 80 and acts on the piston 50 for movement from the top to the bottom in FIG. 2. As can be seen from FIG. 4, a further radial bore 132 is arranged at the upper end of the cylinder housing 46 between the threaded bores 70 and 72, which radial bore forms a second control pressure port. This bore 132 is connected to the annulus 82 between the cylinder sleeve 80 and the wall of the bore 66. Compressed air, which is supplied to this control pressure inlet, flows through the annulus 82 downwards and then through the sections 81 into the lower portion of the cylinder sleeve 80. Thus, this compressed air acts on the piston 50 at the bottom.

The bore 130 is connected to a port 134 of a 4/2-directional control valve. The bore 132 is connected to the 4/2-directional control valve 136 with a port 138. A further port of the 4/2-directional control valve 136 is connected to a source of compressed air 140. The fourth port of the 4/2-directional control valve 136 is connected to atmosphere through a conduit 142. The 4/2-directional control valve 136 is formed as a solenoid valve and can be actuated by a magnet winding 144.

A hose 146 is located at the end 102 of the suction tube carrier 62, which hose is guided to a suction pump 148. The suction pump 148 delivers into an exhaust hood.

A control 150 controls the magnet winding 144, the pump 148 and a power supply 152 for the graphite furnace 10.

The described arrangement operates, controlled by the control 150, as follows:

At first, the 4/2-directional control valve 136 is changed over from the illustrated valve position into the other valve position. The compressed air is supplied to the underside of the piston 50. The piston rod 54 presses the suction tube carrier 62 upwards. Thereby, the suction tube carrier 62 lifts the suction tube portion 64 out of the graphite furnace 10. At the same time, the suction tube 40 is pivoted away backwards from the opening 18 due to the steeply-helical form of the guiding slots. Therefore, the opening 18 lies open. Sample can be dosed through the opening 18 into the graphite furnace 10. The pump 148 and the power supply 152 of the graphite furnace 10 are switched off.

Then the 4/2-directional control valve 136 is changed over into the illustrated valve position. Thereby, the compressed air is supplied to the top to the piston 50. The suction tube carrier 62 is lowered. At first it is returned to the front, such that the suction tube 40 is aligned with the opening 18. Then the suction tube sinks into the graphite furnace 10 in the way illustrated in FIG. 1. Thereby, the end of the suction tube 40 is arranged directly opposite the introduced sample 38. Now the power supply 152 is switched on, such that the graphite furnace 10 is heated up to a drying temperature. At the same time, the pump 148 is switched on by the control 150. The solvent in the sample 38 is vaporized. The solvent vapors are sucked off at once by the suction tube 40. Subsequently the graphite furnace 10 is heated up to charring temperature with the pump 148 continuing to operate. Thereby, decomposition products appear as smoke. Also these decomposition products are sucked off through the suction tube 40.

Thereby a shortening of the drying and charring time results. That shortens the total time, which is required for an analysis. Solvent vapors or smoke or the like are directly sucked off from the sample 38. They need not flow over contacts or cooler wall portions of the graphite furnace 10. That reduces the risk, that material from the drying and charring step condenses at such portions and leads to a falsification of the subsequent measurements. Because the graphite furnace is heated up during a shorter time with each analysis, the useful life of the graphite furnace, consequently the number of the analyses, which can be carried out with a graphite furnace, is increased.

Subsequently the pump 148 is switched off. The valve 136 is changed over into the other valve position, in which compressed air is guided under the piston 50. The suction tube 40 is retracted, as described, from the graphite furnace and pivoted away from the opening 18. The power supply 152 is controlled to heat the graphite furnace 10 up to atomizing temperature. Now a cloud of atoms develops in the graphite furnace 10. The measuring light beam 154 of a spectrometer (not illustrated in detail) emerges from a hollow cathode lamp 156, passes through this cloud of atoms and impinges upon a detector 158. The spectrometer determines, again controlled by the control 150, the absorption, to which the measuring light beam 154 is subjected in the cloud of atoms. Therefrom, the concentration of the element looked for can be determined. That is prior art technique and therefore is not described in detail.

After the measurement has been carried out the graphite furnace 10 remains in the heated state. It is still heated further up to a heating out temperature, if necessary. The suction tube 40 is lowered with its tip 42 into the graphite furnace 10. The pump 148 remains switched on. In this way, also the tip of the suction tube is heated out. The vacuum generated by the pump 148 ensures, that vapors developing during the heating out process are sucked off.

Subsequently the decribed cycle starts anew with a new sample.

We claim:

1. Method for analyzing samples by means of atomic absorption spectroscopy using electrothermal atomization of the samples, comprising the method steps of:
   (a) introducing a liquid sample into a furnace containing a lateral opening;
   (b) inserting a suction tube into said lateral opening of said furnace;
   (c) connecting said suction tube to a vacuum source;
   (d) thereafter, heating the furnace to a predetermined drying temperature for drying the liquid sample introduced into said furnace;
   (e) during said step of heating said furnace to said predetermined drying temperature, sucking off vapors formed in the furnace, through said suction tube under the action of said vacuum source;
   (f) subsequently heating said furnace to a predetermined atomizing temperature for forming a cloud of atoms in the furnace from the dried sample;
   (g) directing a measuring light beam containing resonance spectral lines of a desired element through the cloud of atoms; and
   (h) measuring the atomic absorption of said measuring light beam by the atoms of the desired element in said cloud of atoms.

2. Method as claimed in claim 1, further comprising the steps of:
   (a) after the step of heating the furnace to said predetermined drying temperature, heating the furnace to a predetermined charring temperature at which chemical compounds in the dried sample are decomposed, and
   (b) during said step of heating said furnace to said predetermined charring temperature, sucking off smoke and decomposition products through said suction tube under the action of said vacuum source.

3. Method as claimed in claim 2, further comprising
   (a) introducing the sample into the furnace (10) through said lateral opening which constitutes a sample introduction opening and
   (b) introducing the suction tube (40) into the sample introduction opening (18).

4. The method as claimed in claim 3, further comprising retracting the suction tube (40) from the opening, while the furnace (10) is heated up to the atomizing temperature, and the atomic absorption is subsequently measured.

5. The method as claimed in claim 4, further comprising introducing the suction tube (40), following the measurement with the furnace heated up, again into the opening (18) for heating the furnace in order to drive out sample residues.

6. The method as claimed in claim 5, further including supplying vacuum to the suction tube (40) during the heating of the furnace for driving out said sample residues.

7. An apparatus for analyzing samples by means of atomic absorption spectroscopy, comprising
   (a) a tubular furnace (10) for the electrothermal atomization of samples with a longitudinal bore (24) and a central, lateral opening (18),
   (b) means (125) for passing electric current through the furnace (10) in intensity steps corresponding to different heating steps during said electrothermal atomization,
   (c) means for directing a measuring light beam through the longitudinal bore (24) to a detector exposed to the measuring light beam,
   (d) a suction tube (40) arranged to be introduced into the furnace (10) through the lateral opening (18),
   (e) means (148) for generating a vacuum in the suction tube (40),
   (f) a mechanism for introducing the suction tube (40) into the opening (18) of the furnace (10) and for retracting the suction tube (40) from the furnace (10) and
   (g) a control device (150) for coordinating the movement of the mechanism, the heating steps of the furnace (10) and the means (148) generating a vacuum.

8. An apparatus as claimed in claim 7, comprising means for imparting a rotary movement by the mechanism, after having retracted the suction tube (40) from the opening (18) of the furnace (10), such that the opening (18) lies open for the sample introduction, when the suction tube (40) is retracted.

9. An apparatus as claimed in claim 8, wherein the mechanism for moving the suction tube (40)
   (a) comprises a guiding sleeve (56), which has two diametrically opposite, steeply helical guiding slots (58,60), and
   (b) a suction tube carrier (62), which is guided in the guiding slots (58,60) and carries the suction tube (40), and
   (c) means (50,136,140) for longitudinally moving the suction tube carrier (62) along the guiding sleeve (56), in combination with a rotary movement about the axis of the guiding sleeve due to the curvature of the guiding slots (58,60).

10. An apparatus as claimed in claim 9, wherein
   (a) the suction tube carrier (62) has an annular portion (94) and an integrate handle (96),
   (b) the handle (96) is guided in the guiding slots (58,60) and (c) the suction tube (40) is held at the annular portion (94).

11. An apparatus as claimed in claim 10, wherein a cylindrical suction tube portion (64) is held in the annular portion (94) and, at its end, carries the suction tube (40) to be introduced into the furnace.

12. An apparatus as claimed in claim 11, wherein the suction tube (40) is made of graphite.

13. An apparatus as claimed in claim 11 or 12, wherein the suction tube (40) has a conically tapering end (44), to which a cylindrically tubular tip (42) is added at the furnace side.

14. An apparatus as claimed in claim 13, wherein the suction tube (40) has a section (128) provided with webs.

15. An apparatus as claimed in claim 14, wherein
(a) communicating longitudinal passages (124,116) extend through the suction tube (40) and the suction tube portion (64),
(b) a longitudinal passage (104) extends through the handle (96) of the suction tube carrier (62) and starts in the inner wall of the annular portion (94),
(c) the longitudinal passage of the suction tube portion (64) is connected to the longitudinal passage (104) of the handle (96) and
(d) the longitudinal passage (104) of the handle (96) is connected to the suction pump (148) through a connection hose (146).

16. An apparatus as claimed in claim 15, wherein
(a) the suction tube carrier (64) engages the annular portion (94) with a collar on one side and extends through the opening of this annular portion (94),
(b) a threaded sleeve (110) is screwed upon the suction tube portion (64) and engages the annular portion (94) on the opposite side with a flange (112), such that a closed annulus is formed inside the annular portion (94) and around the suction tube portion (64),
(c) the longitudinal passage (116) of the suction tube portion (64) is connected to this annulus through a transverse bore and
(d) the longitudinal passage (104) of the handle (96) ends in this annulus.

17. An apparatus as claimed in claim 16, wherein the means for moving the suction tube carrier (62) have a pneumatically actuated piston (50) along the guiding sleeve (56).

18. An apparatus as claimed in claim 17, wherein the means for moving the suction tube carrier (62) comprise
(a) a cylinder housing (46) with a bore (66) and
(b) a cylinder sleeve (80) coaxially held in the bore (66) of the cylinder housing (46) at one end, in which cylinder sleeve the piston slides, a holding device (52) of the cylinder sleeve (80) separating the annulus formed between the wall of the bore (66) and the cylinder sleeve (80) from the interior space of the cylinder sleeve (80) located on one side of the piston (50), and, further, the annulus being connected to the interior space of the cylinder sleeve (80) located on the other side of the piston through sections (81) of the cylinder sleeve (80), and
(c) control fluid can optionally be applied to the annulus or to the interior space located on the said one side of the piston (50) through ports (130,132) and a valve (136).

19. Device as claimed in claim 18, characterized in that the guiding sleeve (56), coaxial to the cylinder sleeve (80), is connected to the cylinder housing (46).

* * * * *